United States Patent [19]

Tsushima et al.

[11] Patent Number: 5,166,425
[45] Date of Patent: Nov. 24, 1992

[54] S-DIFLUOROMETHYLHOMOCYSTEINES, PREPARATION PROCESS, AND SELECTIVE INSECTICIDES CONTAINING THEM

[75] Inventors: Tadahiko Tsushima, Osaka; Shoichi Ishihara, Hyogo, both of Japan

[73] Assignee: Shionogi & Co., Ltd., Osaka, Japan

[21] Appl. No.: 706,266

[22] Filed: May 28, 1991

Related U.S. Application Data

[62] Division of Ser. No. 424,369, Oct. 19, 1989, abandoned.

[30] Foreign Application Priority Data

Oct. 25, 1988 [JP] Japan .................................. 63-268733

[51] Int. Cl.$^5$ .............................. C07C 51/02
[52] U.S. Cl. ................................... 562/559; 562/556; 562/605
[58] Field of Search ............... 562/555, 556, 603, 605, 562/559, 553, 602

[56] References Cited

PUBLICATIONS

Tsuji et al., "J. Antibiotics", XXXVIII(4), 466–477 (1985), Synthesis and Antibacterial Activity of 6315-S, A New Member of the Oxacephem Antibiotic.

Hine et al., "J. Am. Chem. Soc.", 79, 5493 (1957), Methylene Derivatives as Intermediates in Polar Reactions.

Hudlicky, "Chemistry of Organic Fluorine Compounds, 2nd. Ed.", p. 444, Ellis Horwood Ltd., Chichester, England (1972).

Primary Examiner—Marianne M. Cintins
Assistant Examiner—Margaret Argo
Attorney, Agent, or Firm—Wenderoth, Lind & Ponack

[57] ABSTRACT

A compound of the formula:

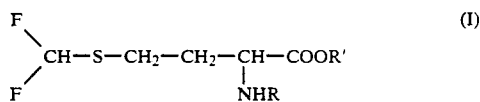

wherein R and R' each is hydrogen or a protecting group, or acid addition salts thereof, useful as a selective insecticide.

2 Claims, No Drawings

S-DIFLUOROMETHYLHOMOCYSTEINES, PREPARATION PROCESS, AND SELECTIVE INSECTICIDES CONTAINING THEM

This is a Rule 60 Divisional of Ser. No. 07/424,369 filed Oct. 19, 1989 now abandoned.

BACKGROUND OF THE INVENTION

1. Field of the Invention

The present invention relates to novel S-difluoromethylhomocysteines and selective insecticides containing them as an active ingredient.

2. Prior Art

Methionine is one of essential amino acids, and both L-type and D-type are effective. Methionine can be used for the treatment for hepatitis and toxicoses as a lipophilic nutrient. But no methionine derivatives showing insecticidal activity have heretofore been reported in any literature.

SUMMARY OF THE INVENTION

Aphides are frequently regarded as harmful insects against crops and horticultural plants. Organophosphate insecticides such as malathion and pirimicarb are used as practical insecticides against such aphides. But the aphides possessing tolerance against these insecticides are increasing. Considering said matter, the present inventors have investigated development of insecticides effective against the aphides possessing tolerance. And the inventors have found that the difluoromethylhomocysteines are effective against the harmful insects mentioned above, and the present invention is based on this finding.

DETAILED DESCRIPTION

The present invention relates to compounds of the formula:

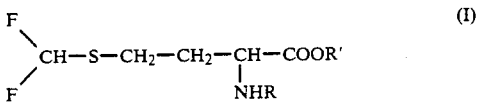

wherein R and R' each is hydrogen or a protecting group, or acid addition salts thereof.

In this invention, a protecting group means amino- or carboxy-protecting group. Amino-protecting group means carbamate type protecting groups, such as tert-butyloxycarbonyl (BOC), p-biphenylisopropyloxycarbonyl (Bpoc), diisopropylmethoxycarbonyl (Dipmoc), or benzyloxycarbonyl (Z), aralkyl ones such as trityl or benzyl, and acyl ones such as acetyl or trifluoroacetyl. Carboxy-protecting group means alkyl such as methyalkyl such as methyl, ethyl, propyl, or butyl, aralkyl such as benzyl or benzhydryl, and pivaloyloxymethyl.

The compound of this invention can be prepared by the following Methods A and B.

Method A
(Synthesis of racemate)

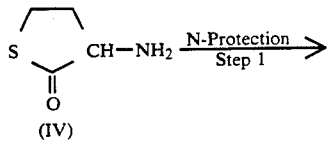

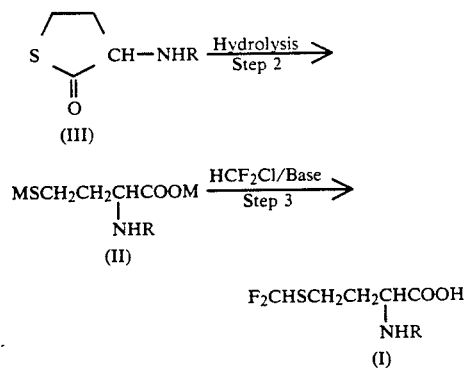

wherein M means alkali metal, and R has the same meaning as defined above.

Step 1

L-Homocysteinethiolactone (IV) is subjected to N-protecting reaction in a conventional manner. This is a process to introduce amino-protecting group such as BOC, Z, trityl, trifluoroacetyl, or acyl into the compound (IV) (M. Bodanszky and A. Bodanszky, "The Practice of Peptide Synthesis" Springer-Verlag, Tokyo, 1984, and Izumiya, et al., "Peptide Synthesis" Maruzen, Tokyo, 1985.). For the introduction of the protecting groups, BOC, trityl, p-biphenylisopropyloxycarbonyl (Bpoc), and diisopropylmethoxy carbonyl (Dipmoc), or other acid sensitive ones, the reaction is performed in an appropriate solvent at $-100°$ to $50°$ C., preferably at $-50°$ C. to room temperature. As reagents for introducing BOC, there are exemplified di-tert-butyl dicarbonate, tert-butyloxycarbonyl chloride, tert-butyloxycarbonyl azide, tert-butyl-4,6-dimethylpyrimidyl-2-thiolcarbonate, and 2-(tert-butoxycarbonyloxyimino)-2-phenylacetonitrile. Trityl chloride can be used for introducing trityl. If necessary, a base can be added. As the base there are exemplified organic bases such as triethylamine, pyridine, or the like, and inorganic bases such as sodium hydrogen carbonate, sodium carbonate, sodium hydroxide or the like. As the solvent there are exemplified alcohols, ethers, methylene chloride, chloroform etc. These amino-protecting groups have some advantages for avoiding racemization and for facile acidic cleavage. When the protecting group is Z group, the compound (IV) is reacted with a reagent such as benzyloxycarbonyl chloride in an appropriate solvent in the presence of a base at $0°$ to $100°$ C., preferably at a temperature around room temperature. As the base used for the reaction there are exemplified organic bases such as triethylamine or the like and inorganic bases such as sodium hydroxide, sodium hydrogencarbonate or the like. The same solvent mentioned above can be used, too.

Step 2

N-Protected-homocysteinethiolactone (III) obtained above is subjected to hydrolysis to give the dialkali metal salt (II). This reaction is performed in an appropriate solvent at $0°$ to $100°$ C. for several minutes to several hours. As alkali used for the reaction there are exemplified sodium bicarbonate, potassium carbonate, potassium t-butoxide, and sodium hydride. As the solvent used for the reaction there are exemplified water, alcohols, or aqueous alcohols.

Step 3

Alkali metalic salt (II) obtained above is reacted with chlorodifluoromethane in the presence of a base to give the objective compound (I). Difluoromethylation of thiols are documented in J. Hine et al, J. Am. Chem. Soc., 79, 5493 (1957); T. Tsuji et al, J. Antibiotics, X X X VII, 466 (1985); M. Hudlicky, "Chemistry of Organic Fluorine Compounds," 2nd. Ed., Ellis Horwood Ltd., Chichester, England, 1972, p 444. But these methods are restricted only to the compound having simple functional groups, and there is no report that said methods have been applied to amino acids or compounds possessing the free carboxy group. Accordingly it is to be emphasized that novel difluoromethylhomocysteine (I) can be conveniently prepared hereby in good yield. The product (I) can be subjected to N-deprotection of amino group and/or esterification of carboxy group, if necessary. When the N-protecting group is benzyloxycarbonyl, it can be removed by hydrogenation or reacting with HBr/AcOH in a conventional manner. When the protecting group is BOC, it is removed by reacting with HBr/AcOH, trifluoroacetic acid/organic solvent (e.g. ethers, methylene chloride, chloroform, etc.), or HCl/organic solvent (e.g. alcohols, methylene chloride, chloroform, etc.). When the protecting group is trityl, it is easily removed by treatment with acids such as acetic acid, trifluoroacetic acid, formic acid, hydrochloric acid, etc. Further, the esterification of carboxy is carried out in an appropriate solvent in a conventional manner, for example, acid-alcohol, diazo compound, thionyl chloride-alcohol, acid halide-base-alcohol or the like. As the solvent, there are exemplified alcohols, THF (tetrahydrofuran), ether, and methylene chloride, etc. The reaction is performed at a temperature $-20°$ to $100°$ C., preferably at a temperature $0°$ C. to room temperature. The compound (I) of the present invention obtained in this method, however, is a complete racemate. Even if as a starting material was used an optically active L-homocysteine thiolactone (IV), the resulting product is a racemate in this method. It is caused by the racemization taking place in Step 2. Thus, the present inventors have investigated catalytic hydrolysis using Ag, Hg, and Cu salts as catalysts [S. Masamune, et al., J. Am. Chem Soc., 97, 3515 (1975)] for avoiding racemization in Step 2, but these attempts failed. Thus, development of another method for preparing such an optically active substance will be shown below as Method B.

Method B (Asymmetric synthesis of L-form)

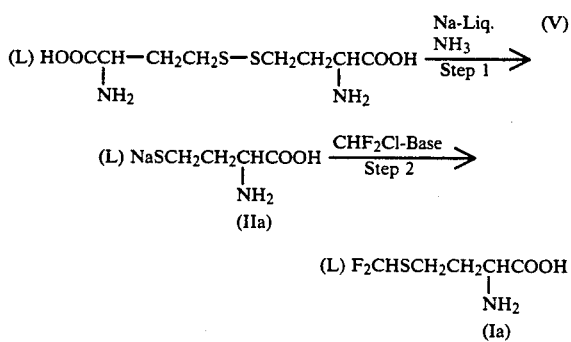

Step 1

This step is directed to a process for preparing L-homocysteine sodium salt (II a) by subjecting L-homocystine (V) to liquid ammonium-sodium reduction in a conventional manner (K. Ramalingam and R. W. Woodard, J. Org. Chem., 1984, 49, 1291.). L-Homocysteine sodium salt (II a), which is a useful intermediate for the chemistry of amino acid peptides, can be obtained without racemization by this reaction. It is recommended that isolation, purification, or preservation of the intermediate (II a) would be carried out under anaerobic conditions, preferably under nitrogen atmosphere, because of its susceptibility to decomposition in the air (due to $CO_2$ or $O_2$).

Step 2

The compound (II a) obtained in Step 1 is reacted with chlorodifluoromethane in the presence of a base to give the compound (I a) of the present invention. Thus, it has been found that optically active L-difluromethylhomocysteine (I a) can be prepared in one step without racemization in this reaction. Accordingly, the reaction is considered as excellent diastereo-selective synthesis of the product (I a). It is recommended that the reaction be performed by carefully avoiding the introduction of air.

The following examples, reference examples and formulation are shown to clarify the practical embodiments of this invention.

EXAMPLE 1

A solution of 1.38 g (6.35 mmol) of N-tert-butyloxycarbonylhomocysteinethiolactone (III) in 8 ml of ethanol is mixed with 6.67 ml of 2N-NaOH. The mixture is stirred at room temperature for 1 hour and concentrated to give white powder. It is dried in a desiccator for 2 days. The resulting powder (II) (279 mg, 1 mmol) is dissolved in 2 ml of ethanol and mixed with chlorodifluoromethane at room temperature under stirring. The mixture is stirred for 8 hours, neutralized with 1N-HCl under ice-cooling, and concentrated under reduced pressure. The residue is basified with 0.5N-NaOH and washed with ether. The washing is acidified to pH 2.0 with 1N-HCl, and the mixture is salted out and extracted three times with ethyl acetate. The organic layer is washed twice with saturated brine. And the solution is dried over magnesium sulfate and concentrated under reduced pressure to give N-BOC-difluoromethylhomocysteine (I-1) as an oily substance.

$^1$HNMR $\delta$(CDCl$_3$): 1.43 (s, 9H, t-Bu); 1.80–2.40 (m, 2H); 2.45–3.00 (m, 2H); 4.40 (br.m, 1H); 5.33 (br.m, 1H); 6.8 (t, 1H, J=5.7 Hz)

The compound obtained above is converted into benzhydryl ester and chromatographed on a column of silica gel HPLC (Lobar B®) eluting with benzene/ethyl acetate (4/1 v/v) to give 269 mg (Yield: 59.6%) of the ester compound.

The compound obtained above is deprotected in trifluoroacetic acid/anisole to give objective amino compound. It is subjected to desalting with Dowex-50W X8 to give 77 mg (Yield: 43%) of (DL)-difluoromethylhomocysteine. mp.>195° C. (dec.)

$[\alpha]_D^{25}$ 0°±0.4° (c, 1.002, 4N-HCl)

EXAMPLE 2

Into a solution of 2.04 g (10.56 mmol) of L-homocysteine sodium salt in 18 ml of ethanol is vigorously bubbled chlorodifluoromethane at room temperature while keeping the dropwise addition of potassium tert-butoxide in ethanol (2.03 g, 2.01 mmol/12 ml) placed in funnel over 1 to 2 hours. After the addition of the base, chlorodifluoromethane is introduced for additional 1 hour and then the solution is acidified (pH 4.3) with 1N HCl under ice-cooling and concentrated under reduced pressure. The residue is well dried by distilling off the freshly added ethanol twice and again 200 ml of methanol added to precipitate inorganic salts. The insoluble salts are filtered off and the filtrate is concentrated to give 1.7 g of the residue. The residue is purified by column chromatography successively on ion exchange resin Dowex 50W-X8 using $1N-NH_3$ as an eluent, and on HP-20 using an aqueous methanol as an eluent to give 1.1 g (Yield: 56%) of the desired compound L-difluoromethylhomocysteine. mp. > 195° C. (dec.)

$[\alpha]_D^{25}$ +23.4°±0.8° (c, 0.822, 4N-HCl)

$^1$HNMR (D$_2$O, 200 MHz) δ: 2.33 (m, 2H, β-C$\underline{H}$), (t, 2H, J=7.8 Hz, γ-C$\underline{H}_2$); 3.84 (t, 1H, J=6.4 Hz, α-C$\underline{H}_2$); 7.07 (t, 1H, J=55.8 Hz, C$\underline{H}$F$_2$)

IR (KBr): 3400 (m); 3200–2400 (br, s); 1585 (br, s); 1513 (s); 1408 (s); 1326 (m); 1015 (s); 765 (m) cm$^{-1}$

Mass m/z: 186 (MH$^+$), 167 (MH$^+$-F), 140 (M$^+$-COOH), 134 (M$^+$-CHF$_2$), 111 (F$_2$CHSCH$_2$CH$_2$), 97 (F$_2$CHSCH$_2$), 74 (M$^+$-F$_2$CHSCH$_2$CH$_2$)

Anal Calcd. (%) for C$_5$H$_9$NF$_2$S C, 32.43; H, 4.90; N, 7.56; F, 20.52; S, 17.31; Found: C, 32.31; H, 4.87; N, 7.54; F, 20.21; S, 17.60.

EFFECT OF THE INVENTION

1. Test Method

Preparation of a test solution

A solution of the compound is diluted with distilled water containing Tween 20 ® at a concentration of 100 ppm to prepare a predetermined concentration of the test solution. Malathion emulsion and pirimicarb wettable powder are diluted with distilled water to prepare a predetermined concentration of the test solution, respectively.

Aphides tested

Myzus persicae (URR-O type) distributed from Chiba University, which were reared for succesive generations, were used as a group of sensitive strains. Myzus persicae resistant to malathion and pirimicarb which were collected from Aburahi Laboratory of Shionogi & Co., Ltd. and reared for succesive generations while selecting those resistant to these drugs were used as a group of resistant strains.

Experiment

A polyethylene cup (diameter 6 cm, depth 4 cm) was filled with 0.3% agar gel and a piece of Chinese cabbage leaf (3×3 cm) was placed on the gel. One apterous adult of Myzus persicae was put on the leaf and allowed to keep at 25° C. for 24 hours to make larviposition. After removal of the adult, 2 ml of the test solution was applied to the foliage under a rotary sprayer; and larvae of Myzus persicae was allowed to keep at 25° C. for 48 hours. Then the mortality of the larvae was determined and the value of LC$_{50}$ was calculated by the method of Billis. [Bliis, Ann. Appl. Biol., 22, 134;307 (1935)].

Result

TABLE 1

| | Mortality (%) against Myzus persicae | | |
|---|---|---|---|
| | Concentration | Mortality (%) | |
| Compound | (ppm) | Sensitive strain | Resistant Strain |
| | 250 | 100 | 100 |
| Compound | 125 | 100 | 100 |
| I$^a$ | 62.5 | 57.1 | 100 |
| | 31.3 | 4.8 | 54.2 |
| | 15.6 | 8.7 | 0.0 |
| | 7.8 | 0.0 | 5.0 |

*$^1$: L-Difluoromethylhomocysteine

TABLE 2

| The value of LC$_{50}$ against Myzus persicae | | |
|---|---|---|
| Test | LC$_{50}$ (ppm) | |
| Compound | Sensitive Strain | Resistant Strain |
| Compound | 52.9 | 27.1 |
| I$^a$ | (48.1–58.3)*$^2$ | (24.8–29.7) |
| malathion | 136.0 | 2000< |
| | (122.7–150.8) | |
| pirimicarb | 8.2 | 1920< |
| | (7.2–9.0) | |

*$^2$: ( ) means 95% confidence limit

What we claim is:

1. A process for preparing the compound of the formula:

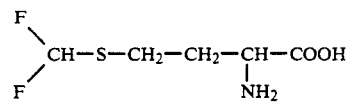

or acid addition salts thereof, which comprises reacting L-homocysteine sodium salt prepared from L-homocystine with chlorodifluoromethane, without racemization, in the presence of potassium tert-butoxide.

2. The process of claim 1 wherein the reaction with chlorodifluoromethane is performed in the substantial absence of air.

* * * * *